US011913948B2

(12) United States Patent
Chiu

(10) Patent No.: US 11,913,948 B2
(45) **Date of Patent: *Feb. 27, 2024**

(54) METHOD FOR ACCURATE DIAGNOSIS OF A DISEASE TARGETING BIOMARKERS IN LIQUID BIOPSY

(71) Applicant: PHASE SCIENTIFIC INTERNATIONAL, LTD., Hong Kong (CN)

(72) Inventor: Yin To Chiu, Hong Kong (CN)

(73) Assignee: PHASE SCIENTIFIC INTERNATIONAL, LTD., Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/663,670

(22) Filed: May 17, 2022

(65) Prior Publication Data

US 2022/0276239 A1 Sep. 1, 2022

Related U.S. Application Data

(62) Division of application No. 16/497,530, filed as application No. PCT/US2018/024796 on Mar. 28, 2018, now Pat. No. 11,366,111.

(60) Provisional application No. 62/560,180, filed on Sep. 18, 2017, provisional application No. 62/478,021, filed on Mar. 28, 2017.

(51) Int. Cl.
*G01N 33/543* (2006.01)
*G01N 33/574* (2006.01)

(52) U.S. Cl.
CPC ..... *G01N 33/54386* (2013.01); *G01N 33/574* (2013.01)

(58) Field of Classification Search
CPC ........... G01N 33/54386; G01N 33/574; G01N 33/57488; G01N 2333/471; C12Q 1/6886
See application file for complete search history.

(56) References Cited

U.S. PATENT DOCUMENTS

| | | | |
|---|---|---|---|
| 6,132,763 | A | 10/2000 | Fisher |
| 6,399,385 | B1 | 6/2002 | Croyle et al. |
| 7,626,017 | B2 | 12/2009 | Laugharn, Jr. et al. |
| 7,666,583 | B2 | 2/2010 | Mor et al. |
| 7,803,405 | B2 | 9/2010 | Keating et al. |
| 9,823,247 | B2 | 11/2017 | Kamei et al. |
| 10,006,911 | B2 | 6/2018 | Kamei et al. |
| 10,359,423 | B2 | 7/2019 | Kamei et al. |
| 10,578,616 | B2 | 3/2020 | Kamei et al. |
| 11,287,426 | B2 | 3/2022 | Kamei et al. |
| 11,327,075 | B2 | 5/2022 | Kamei et al. |
| 2002/0042506 | A1 | 4/2002 | Kristyanne et al. |
| 2005/0077497 | A1 | 4/2005 | Anderson |
| 2006/0025579 | A1 | 2/2006 | Riedl et al. |
| 2006/0166349 | A1 | 7/2006 | Kepka et al. |
| 2007/0161000 | A1 | 7/2007 | Van Alstine et al. |
| 2008/0242825 | A1 | 10/2008 | Devi et al. |
| 2009/0192111 | A1 | 7/2009 | Bader et al. |
| 2009/0286966 | A1 | 11/2009 | Christensen et al. |
| 2010/0174052 | A1 | 7/2010 | Hjorth et al. |
| 2010/0179252 | A1 | 7/2010 | Johansson et al. |
| 2011/0257378 | A1 | 10/2011 | Tran et al. |
| 2011/0263040 | A1 | 10/2011 | Jones |
| 2013/0164825 | A1 | 6/2013 | Christoffel et al. |
| 2014/0221549 | A1 | 8/2014 | Bodkhe et al. |
| 2014/0227712 | A1 | 8/2014 | Horlitz et al. |
| 2014/0228549 | A1 | 8/2014 | Burghoff et al. |
| 2015/0253320 | A1 | 9/2015 | Kamei et al. |
| 2018/0100854 | A1 | 4/2018 | Kamei et al. |
| 2018/0259521 | A1 | 9/2018 | Kamei et al. |
| 2019/0033308 | A1 | 1/2019 | Kamei et al. |
| 2019/0187140 | A1 | 6/2019 | Kamei et al. |
| 2019/0250156 | A1 | 8/2019 | Kamei et al. |
| 2019/0391143 | A1 | 12/2019 | Kamei et al. |
| 2020/0150116 | A1 | 5/2020 | Kamei et al. |
| 2020/0284791 | A1 | 9/2020 | Kamei et al. |
| 2022/0252598 | A1 | 8/2022 | Kamei et al. |

FOREIGN PATENT DOCUMENTS

| | | | |
|---|---|---|---|
| CN | 101679481 | A | 3/2010 |
| CN | 102264901 | A | 11/2011 |
| CN | 102272144 | A | 12/2011 |
| CN | 102421898 | A | 4/2012 |
| CN | 106662582 | A | 5/2017 |
| CN | 110003323 | A | 7/2019 |

(Continued)

OTHER PUBLICATIONS

Ziegler YS, et al. (2014) Plasma membrane proteomics of human breast cancer cell lines identifies potential targets for breast cancer diagnosis and treatment. PLoS One. 9(7):e102341.
Schindler J, et al. (2008) Aqueous polymer two-phase systems for the proteomic analysis of plasma membranes from minute brain samples. J Proteome Res 7(1):432-442.
Spindler KL, et al. (2015) Circulating free DNA as biomarker and source for mutation detection in metastatic colorectal cancer. PLoS One. 10(4):e0108247.
Riedl W, et al. (2008) Membrane-supported extraction of biomolecules with aqueous two-phase systems[J]. Desalination, 224(1-3): 160-167.
Frerix A, et al. (2005) Scalable recovery of plasmid DNA based on aqueous two-phase separation. Biotechnol Appl Biochem. 42(Pt 1):57-66.

(Continued)

*Primary Examiner* — Changhwa J Cheu
(74) *Attorney, Agent, or Firm* — EAGLE IP LIMITED

(57) ABSTRACT

The present invention relates to a method for improving the detection and diagnosis targeting biomarkers using an aqueous two-phase system (ATPS). In one embodiment, the present invention provides a method for improving a diagnostic procedure involving the detection or quantification of one or more biomarkers in liquid biopsy, the method comprises contacting a porous material embedded with ATPS components with a liquid biopsy containing the biomarkers, purifying and concentrating the target biomarkers, and providing a product comprising the target biomarkers for performing the diagnostic procedure.

13 Claims, 1 Drawing Sheet

(56) References Cited

FOREIGN PATENT DOCUMENTS

| | | | |
|---|---|---|---|
| EP | 0268946 | A2 | 6/1988 |
| JP | 2000245460 | A | 9/2000 |
| JP | 2002537106 | A | 11/2002 |
| JP | 2007525222 | A | 9/2007 |
| JP | 2017513015 | A | 5/2017 |
| WO | 0050161 | A1 | 8/2000 |
| WO | 2002057289 | A1 | 7/2002 |
| WO | 2011159537 | A2 | 12/2011 |
| WO | 2014128129 | A1 | 8/2014 |
| WO | 2015134938 | A1 | 9/2015 |
| WO | 2016155888 | A1 | 10/2016 |
| WO | 2017041030 | A1 | 3/2017 |
| WO | 2017214315 | A1 | 12/2017 |
| WO | 2018039139 | A1 | 3/2018 |
| WO | 2018183454 | A1 | 10/2018 |
| WO | 2018183465 | A1 | 10/2018 |
| WO | 2018222972 | A1 | 12/2018 |
| WO | 2019046553 | A1 | 3/2019 |
| WO | 2019046563 | A1 | 3/2019 |
| WO | 2019055926 | A2 | 3/2019 |
| WO | 2019118712 | A1 | 6/2019 |
| WO | 2019143895 | A1 | 7/2019 |
| WO | 2019143943 | A2 | 7/2019 |
| WO | 2019144016 | A1 | 7/2019 |
| WO | 2019144030 | A1 | 7/2019 |

OTHER PUBLICATIONS

Crucho Cic, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou, et al. (2015) Nanoparticle Vesicles with Controllable Surface Topographies through Block Copolymer-Mediated Self-Assembly of Silica Nanospheres, Langmuir, vol. 31(48), 11 pages 13214-13220.

Bashir, et al. (2016) Controlled-release of Bacillus thurigiensis formulations encapsulated in light-resistant colloidosomal micro-capsules for the management of lepidopteran pests of *Brassica* crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

Luechau, Frank, et al. (2009) Primary capture of high molecular weight nucleic acids using aqueous two-phase systems. Separation and purification technology, 66.1: 202-207.

Nazer, Behzad, et al. (2017) Plasmid DNA affinity partitioning using polyethylene glycol-sodium sulfate aqueous two-phase systems. Journal of Chromatography B, 1044-1045, 112-119.

Sorber L., et al. (2017) A Comparison of Cell-Free DNA Isolation Kits: Isolation and Quantification of Cell-Free DNA in Plasma. J Mol Diagn. Jan. 19(1):162-168.

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, PLOS ONE, Dec. 18, 2020, p. e0244271, vol. 15, No. 12.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Ricky Y. T. Chiu, et al., An Aqueous Two-Phase System for the Concentration and Extraction of Proteins from the Interface for Detection Using the Lateral-Flow Immunoassay, PLOS ONE, Nov. 10, 2015, 1-14, PLOS, California, US.

K. Jessie, et al., Protein Precipitation Method for Salivary Proteins and Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 No. 6, IRL Press Limited, Oxford, England.

Donald C Rio, et al., Purification of RNA by SDS solubilization and phenol extraction, Cold Spring Harb Protoc, Jun. 2010, 1-4, vol. 2010 Issue 6, Cold Spring Harbor Laboratory Press, NY, USA.

Zsolt Czimmerer, et al., A Versatile Method to Design Stem-Loop Primer-Based Quantitative PCR Assays for Detecting Small Regulatory RNA Molecules, PLOS ONE, Jan. 31, 2013, 1-10, vol. 8 Issue 1, PLOS, California, US.

Wu et al., "Factors Affecting Aqueous Two-Phase Extraction", Biopharmaceutical Technology (Fourth Edition), Aug. 2015, p. 122-126, China medicine science and technology press.

"Silicone Polyethers—Silsurf", Retrieved from the internet <URL: https://www.siltech.com/products/silicone-polyethers-silsurf/#:~: text=Silicone%20polyethers%2C%20or%20silicone%20surfactants,specific%20properties%20of%20a%20product>. [retrieved on Feb. 17, 2023].

Filip Janku; et al., "A novel method for liquid-phase extraction of cell-free DNA for detection of circulating tumor DNA", Scientific reports, 2021, 11(1): 19653.

| ATPS Type | Polymer/salt | | | | Micellar | | | |
|---|---|---|---|---|---|---|---|---|
| Visualization |  | | | | | | | |
| Concentration Factor | 1 | 30 | 50 | 100 | 1 | 40 | 70 | 100 |

METHOD FOR ACCURATE DIAGNOSIS OF A DISEASE TARGETING BIOMARKERS IN LIQUID BIOPSY

CROSS-REFERENCE TO RELATED APPLICATIONS

This application is a divisional application of U.S. Ser. No. 16/497,530 filed on Sep. 25, 2019, which is the national stage of International Application No. PCT/US2018/024796 filed on Mar. 28, 2018, which claims the benefits of U.S. Ser. No. 62/478,021, filed Mar. 28, 2017 and U.S. Ser. No. 62/560,180, filed Sep. 18, 2017, the entire contents and disclosures of which are hereby incorporated by reference into this application. This application also cites various publications, the entire contents of which are incorporated herein by reference into this application.

FIELD OF THE INVENTION

The present invention relates to a method for improving the detection and diagnosis targeting biomarkers using an aqueous two-phase system (ATPS). In particular, the present invention provides a method for improving the performance of detection and diagnosis targeting biomarkers found in liquid biopsy.

BACKGROUND OF THE INVENTION

Biomarkers are molecular indicators of a specific biological property, a biochemical feature or facet that can be used to measure the presence, severity or progress of a disease or the effects of a treatment. For example, tumor-derived DNA present in the cell-free plasma or serum of cancer patients can be used as a diagnostic biomarker for evaluating a particular type of tumors or cancers in the patient. Very often, different diagnostic biomarkers are specifically related towards different type and form of diseases in the plasma or serum of patients.

Diagnostic tests using biomarkers as molecular indicators do not only detect the presence or absence of the biomarker, but often measure the exact concentration of the biomarker to determine whether an abnormal condition exists. Because of the requirement for accuracy, the process of sample collection, preparation, and analysis are often complicated and time consuming Currently, blood-based assays for biomarker presence or activity are considered to be the “gold standard” for biomarker-type assays.

In particular to cancers, an accurate detection and quantification of cancer biomarkers are particularly important for an accurate and sensitive diagnosis of the cancer as well as monitoring of the treatment, in both the onset and advanced stage of the cancer. Cancer biomarkers may be present in minute amount in the early stage of cancer while the profile of cancer biomarkers may become more complex and confusing as the cancer progresses to an advanced stage especially where metastasis occurs. An accurate and reliable drug response analysis based on cancer and drawbacks of a particular treatment must be evaluated to devise the best treatment strategy for the patients.

It has been a huge challenge to detect the existence of an analyte which has an extremely minute concentration. The analyte can be a biomarker of a cancer disease such as a cell free DNA (cfDNA), Alpha-fetoprotein (AFP) for hepatocellular carcinoma cancer, Cancer Antigen such as CA15-3 for Breast cancer and so on which may exist in the blood, saliva, urine or other body fluids of the patients. Many of the existing diagnostic or detection methods may falsely report that the analyte does not exist if the concentration is too low. The gold standard of diagnostics such as PCR and ELISA may produce a false negative result if the targeted analyte has extremely low concentration. Moreover, there are various biomolecules present in blood, serum and plasma which will interfere and affect the diagnostics accuracy such as peptides, oligosaccharides, ligands, small molecule and natural products. Effective purification and concentration method is highly desired.

There are purification products widely used in literature to concentrate cfDNA and other cancer biomarkers. However, these expensive product kits are limited by the maximum sample volume they can process, as well as the amount of DNA that can be purified before clogging in the blood samples. A method to concentrate the analyte by porous material embedded with ATPS has been disclosed in patent WO2017041030. Unfortunately, the fold of concentration was only about 10-fold, which hardly satisfies the requirement for an accurate and sensitive diagnosis of cancer. An improved method and device to achieve higher concentration of target biomarkers is highly desired.

To overcome these limitations, the present invention provides an improved method to purify and concentrate the target analytes (biomarkers) present in liquid biopsy including blood, serum and plasma for further analysis easily and quickly in a single step without the need of complex equipment. Using porous material embedded with ATPS, the present method can purify biomarkers from liquid biopsy and concentrate the biomarkers for up to 100× or more. Overall, the methods described herein can improve the accuracy, sensitivity and efficiency of the detection and quantification of biomarkers and therefore are capable of improving the performance of various analytical or diagnostic technologies relying on the detection and/or quantification of biomarkers. Many life-threatening diseases are cured if the diseases are detected early.

BRIEF SUMMARY OF THE INVENTION

The present invention relates to a method for improving the detection and diagnosis targeting biomarkers using an aqueous two-phase system (ATPS).

In one embodiment, the present invention provides a method for improving a diagnostic procedure involving the detection or quantification of one or more biomarkers in liquid biopsy, the method comprises contacting a porous material embedded with ATPS components with a liquid biopsy containing the biomarkers, purifying and concentrating the target biomarkers, and providing a product comprising the target biomarkers for performing the diagnostic procedure.

DETAILED DESCRIPTION OF THE INVENTION

Figure 1:
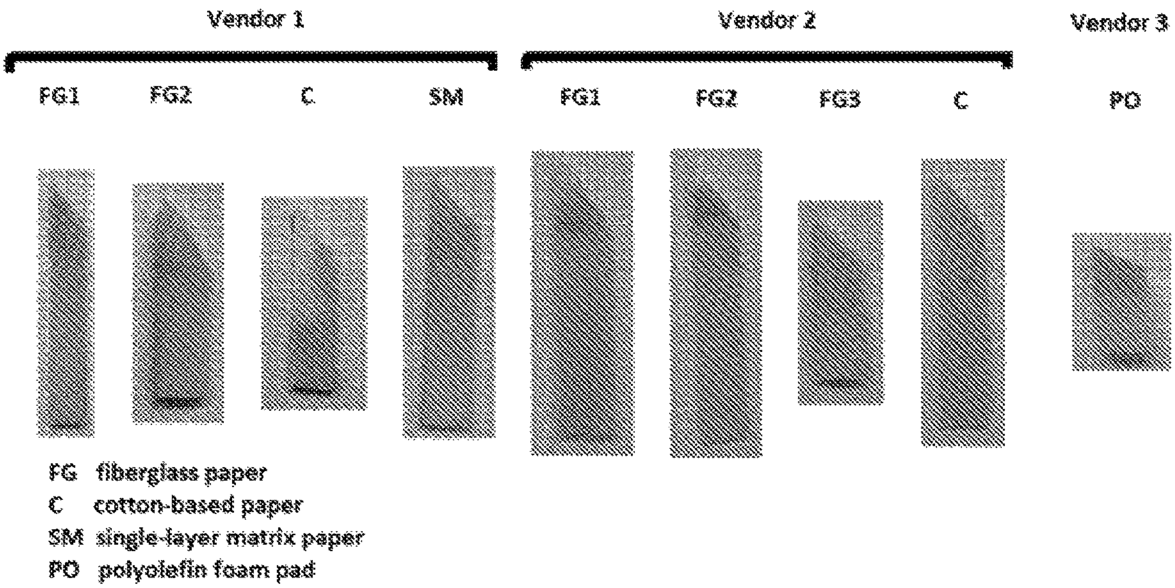
FIG. 1 shows the phase separation using different pre-coated porous materials embedded with ATPS components.

The present invention relates to a method for improving the detection and diagnosis targeting biomarkers in liquid biopsy using an aqueous two-phase system (ATPS).

In the following description, several embodiments of the present invention are described. For purposes of explanation, specific configurations and details are set forth in order to provide a thorough understanding of the embodiments. In addition, to the plural or singular forms of a word and to the extent that orientations of the embodiments are described as, "top", "bottom", "front", "back", "left", "right" and the like, these wordings are to aid the reader in understanding the embodiments and are not meant to be limiting physically. It is apparent to a person skilled in the art that the present invention may be practiced without specific details. The invention will be better understood by reference to the examples which follow, but those skilled in the art will readily appreciate that the specific examples are for illustrative purposes only and should not limit the scope of the invention which is defined by the claims which follow thereafter. It is to be noted that the transitional term "comprising" or "including", which is synonymous with "containing" or "characterized by", is inclusive or open-ended and does not exclude additional, unrecited elements or method steps.

In one embodiment of the present method, ATPS (aqueous two phase system) components are embedded entirely within a porous material, allowing spontaneous phase separation and therefore, purification and concentration of target biomarkers from the sample with only a single-step. The present invention can be applied to various diagnostic or detection technologies that based on the detection or quantification of biomarkers, including but are not limited to Enzyme-Linked Immune Sorbent Assay (ELISA), Polymerase Chain Reaction (PCR), Radioimmunoassay (RIA), proteomic approach and so on.

In one embodiment, the present invention provides a method for improving the performance of diagnosis involving the detection or quantification of a target biomarker in a biopsy using a porous material embedded with an aqueous two-phase system (ATPS). In one embodiment, the present invention comprises the steps of purifying and concentrating the target biomarkers present in a biopsy such as blood, serum and plasma of cancer patient effectively and efficiently. In one embodiment, the purified and concentrated target biomarkers obtained by the present invention are then subject to downstream technologies for the detection or diagnosis of a particular type of disease or a particular health indicator.

Type of Samples and Biomarkers

In one embodiment, the present method is used to improve the performance of a diagnosis involving the detection or quantification of a target biomarker in a sample.

In one embodiment, the present method is applicable to any types of sample containing a biomolecule which is indicative of a disease or a health condition (i.e., a biomarkers). In one embodiment, samples include but are not limited to blood, plasma, serum, tissues, bacteria, viruses, RNA viruses, smear preparations, bacteria cultures, cell cultures (e.g. cell suspensions and adherent cells), urine, saliva, fecal matters, and bodily discharges (e.g. tears, sputum, nasopharyngeal mucus, vaginal discharge and penile discharge), polymerase chain reaction (PCR) mixtures and in vitro nucleic acid modification reaction mixtures.

In one embodiment, the sample is a liquid biopsy taken from a subject including but is not limited to blood, plasma, serum, urine, saliva and various types of bodily discharges (e.g. tears, sputum, nasopharyngeal mucus, vaginal discharge and penile discharge).

In one embodiment, the present methods can separate a target analyte or biomarker from non-target molecules (e.g., small molecules and macromolecules which are typically of natural origin and may interfere with the detection or quantification of target biomarker) in a sample and thereby allows a more accurate detection and diagnosis.

In one embodiment, biomarker subject to the present method is any biomolecule exists in a subject and is indicative of a disease or a health condition in the subject.

In one embodiment, the biomarker is a nucleic acid, a protein or a small molecule.

In one embodiment, the biomarker is a cell-free molecule including but is not limited to a cell-free DNA (cfDNA), a cell-free protein, an exosome and a cell-free molecule circulating in the body fluid of the subject. In one embodiment, the biomarker is a molecule attached to the surface of a cell, or included in a cell.

In one embodiment, the biomarker is a nucleic acid of various types (e.g. DNA including cDNA, RNA including mRNA and rRNA), forms (e.g. single-stranded, double-stranded, coiled, as a plasmid, non-coding or coding) and lengths (e.g. an oligonucleotide, a gene, a chromosome and genomic DNA), originated from the subject or an exogenous agent or both.

In one embodiment, the biomarker is a protein which is a peptide or a polypeptide, including an intact protein molecule, a degraded protein molecule and digested fragments of a protein molecule. In one embodiment, biomarkers include but are not limited to antigens, receptors and antibodies, originated from the subject or an exogenous agent or both.

In one embodiment, the biomarker is a small molecule such as a metabolite. In one embodiment, the metabolite is a disease-related metabolite which is indicative of the presence or extent of a disease or a health condition. In one embodiment, the metabolite is a drug-related metabolite such as a drug by-product of which the level changes in a subject body consuming the drug.

In one embodiment, the target biomarker is originated from the subject himself or herself (e.g. molecules that are derived or released from any organs, tissues or cells of the subject), an exogenous source (e.g. a pathogen such as virus or bacteria associated with a particular disease), or a food or drug taken by the subject.

In one embodiment, the target biomarker is a molecule produced by a tumor or cancer, or by the body of the subject in response to a tumor or cancer.

In one embodiment, the target biomarker is not normally found in healthy subject. In one embodiment, the target biomarker is a molecule that is normally found in a healthy subject but the level of which is indicative of a particular disease or a health condition.

In one embodiment, the target biomarker is a biomolecule which is associated with a tumor or cancer, including but is not limited to, cell-free DNA, alpha-fetoprotein (AFP), Cancer Antigen (CA15-3), cancer Antigen (CA125), Prostate specific antigen BRCA1, Carcinoembryonic antigen, c-erb-2, P16, p53, Aldose reductase, Angiogenin, Annexin A1, B-cell activating factor (BAFF), B-cell lymphoma 2 (BCL2)-like 2, Beta Human chorionic gonadotropin, Ca15-3, Calcyclin, Calvasculin, Cathepsin D, Caveolin-1, Chromogranin A, Alpha-crystallin B chain (CRYAB), Endostatin, Eotaxin-2, Epithelial cell adhesion molecule (EpCAM), Ezrin, fatty acid binding protein 4 (FABP4), Galectin-3, γ-glutamylcysteine ligase regulatory chain (GCLR), Gelsolin, Glucose 6-phosphate (G6P), Glycoprotein 130 (gp130), Glutathione S-transferase Mu 1 (GSTM1), Hepsin, High-mobility group protein B1 (HMGB-1), Insulin-like growth factor binding protein 1 (IGFBP-1), Insulin-like growth factor binding protein 4 (IGFBP-4), Insulin-like growth factor binding protein 5 (IGFBP-5), Insulin-like growth factor binding protein 6 (IGFBP-6), LGL, latency associated peptide (LAP), macrophage stimulating protein (MSP), MHC class I polypeptide-related sequence A (MICA), Nucleoside diphosphate kinase B (NME2), Neuron-specific Enolase (NSE), Osteopontin, Osteoprotegerin, Pepsinogen, Peroxiredoxin, Phosphoserine aminotransferase (PSAT1), Prostate Specific Antigen, Receptor tyrosine-protein kinase erbB-3 (ErbB3), Serpin B3, Vascular smooth muscle cell growth factor R2 (VSGF R2/KDR), Vascular endothelial growth factor R3 (VEGF R3/Flt-4), Thyroglobulin, Tyrosine kinase with immunoglobulin-like and EGF-like domains 2 (TIE-2), Tissue plasminogen activator (tPA), Transforming growth factor beta (TGF-β1), Tumor necrosis factor receptor 1 (TNF-R1), urokinase-type Plasminogen Activator (uPA), urokinase-type Plasminogen Activator Receptor (uPAR), Brcal, Brcall, kallikreins, e-cadherin, Hox peptide, and Engrailed-2.

ATPS (Aqueous Two-Phase System)

In one embodiment, there is provided a two-component ATPS embedded entirely within a porous material for purifying a target biomarker from a sample and concentration of the biomarker. When the ATPS is applied on a porous material (e.g. paper), the two phases of the ATPS separate from each other as the mixed phase solution flows through the porous materials. The resulting phase solutions are of different physicochemical properties and each phase travels through the porous matrix at different rates. Different molecules in a mixture would be distributed differentially between the two phase solutions due to their different properties, and it is possible to separate and concentrate target molecules using ATPS with minimal set up and human intervention. No power or equipment is necessary to bring about the phase separation, as the fluid flow relies purely on capillary action which is based on isothermal-dynamic principles.

The advantage of the invention is that high purity and concentration of the target biomarker can be obtained in a simple way and compatible with downstream application analysis without further step of purification or concentration.

The methods and devices provided herein are robust, inexpensive, simple, easy to handle, safe, user friendly and fast. The present method is able to purify and concentrate the target biomarker and thereby ensures the performance of the downstream applications using the purified and concentrated biomarker will not be affected by impurities in the original sample. Since the present invention does not require any additional power source, complex instrumentation or electronic hardware to operate, it provides a fast and affordable means for rapid analyte isolation and purification.

Because of the unique features described herein, the present invention can purify and concentrate the target biomarker conveniently and rapidly without the use of external power source or complex instrumentation, and is applicable to samples containing the target biomarker in a very low amount, or of a small volume. Furthermore, the present method is readily adaptable to automation including high throughput screening systems.

In one embodiment, the present method is used to purify and concentrate a target biomarker from blood. The present method is able to lyse the blood cells to release their contents, separate the target biomarker from non-target molecules including cell debris, and concentrate the target biomarker simultaneously.

In another embodiment, the present method is used to purify and concentrate a target biomarker from serum or plasma.

In one embodiment of the present method, the target biomarker is retained on the ATPS while non-target materials are left in the liquid system (i.e., original sample plus any non-ATPS components).

In one embodiment, by changing the amounts of ATPS components embedded on the porous material and thereby the volume ratio of the two phases, the target biomarker can be preferentially concentrated in one phase. In one embodiment, the target biomarker is retained in the leading front of the ATPS, which is then collected and optionally further analyzed using appropriate technologies. In one embodiment as illustrated by the examples provided herein, target biomolecule is purified at the top of the porous material embedded with ATPS components and concentrated for up to 50-100 folds as compared to a control stack having no ATPS components.

Design of ATPS-Embedded Porous Material

In one embodiment, the present invention provides a porous material embedded with ATPS components. Various ATPS systems can be used in the present invention, including but are not limited to polymer-polymer (e.g. PEG-dextran), polymer-salt (e.g. PEG-salt), and micellar (e.g. Triton X-114). Porous material may be made of any suitable porous material which can absorb and transfer liquid. Suitable porous materials for this invention include but are not limited to fiberglass paper, cotton-based paper, other types of paper, polymer foams, cellulose foams, other types of foams, rayon fabric, cotton fabric, other types of fabric, wood, stones, and any other materials that can absorb and transfer liquid.

In one embodiment, the porous material is commercially available or manufactured in-house.

FIG. 1 illustrates the ability of several types of porous materials (fiberglass paper, cotton-based paper, single-layer matrix paper and polyolefin foam pad) from three vendors in inducing phase separation when impregnated with ATPS components. Target analytes were indicated by a purple color. As shown in FIG. 1, fiberglass paper FG1 from vendor 1, FG1 and FG2 from vendor 2 and polyolefin foam pad from vendor 3 were the best at concentrating analyte with a strong leading purple front.

Adjustment of Concentration Factors

In one embodiment, the relative amounts of ATPS components in the porous material can be changed. The volume ratio of the two components of ATPS are controlled so as to concentrate the target biomarker preferentially in one component.

To better quantify the phenomena associated with the present invention, an assay was developed to evaluate the correlation between the relative amounts of ATPS components embedded on the porous material and the fold of concentration achieved. With this, the concentration factor can be selected and fine-tuned by adjusting the relative amount of the ATPS components as needed.

In one embodiment, to integrate the ATPS components into the porous material, the ATPS components were solubilized in water (or appropriate buffer) and applied on the porous material in certain ratios. The porous materials were then placed in a lyophilizer to remove water, resulting in the ATPS components embedded directly on the porous material. Upon introduction of the sample to the porous materials, the ATPS components instantly undergo rehydration and thereby separate the molecules in the sample and concentrate the target analyte at the front of the fluid flow without any external power or equipment to provide a driving force.

Figure 2:
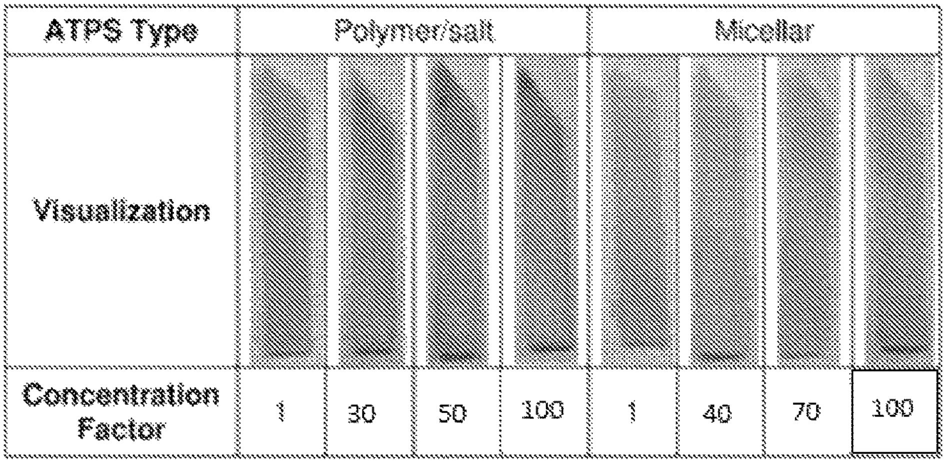
FIG. 2 shows one embodiment of the present invention in which biomolecules were concentrated in the leading front of the ATPS on the porous material up to various concentration factors.

As illustrated in FIG. 2 where two combinations of ATPS (micellar-based and polymer/salt-based ATPS) were tested, the concentration of a targeted analyte could be achieved up to 100× or more. Same amount of purple-colored analyte was loaded to porous materials embedded with varying amount of ATPS components as well as porous materials without ATPS components as a control. For the control, the analyte was homogenously distributed throughout the porous material with the light purple color. On the other hand, introduction of ATPS components into the porous materials allows for concentration of the analyte at the leading front of the fluid flow, as signified by a darker purple color. The data herein demonstrated that the concentration factors achieved were between 30× and 100×. More importantly, the data herein demonstrated that by adjusting the ratios of ATPS components embedded on the porous material, the present invention can adjust the concentration factor as needed. Furthermore, the data indicated that multiple ATPS components (a polymer/salt system and micellar system) incorporated into porous material can achieve purification and concentration of analyte. Other polymer/salt, micellar, and polymer/polymer systems can be likewise implemented with further optimization.

In one embodiment, the porous fiberglass paper is impregnated with ATPS which is made of polymer to polymer based PEG-dextran. When a sample containing a plurality of analytes is poured onto the ATPS on the porous fiberglass paper, the impregnated porous fiberglass paper preferentially causes the analyte-containing ATPS component to flow ahead of the other ATPS component. Therefore, the targeted analyte is concentrated in the analyte-containing ATPS component at the front of the fluid flow.

In one embodiment, the porous fiberglass paper is pretreated with ATPS which is made of polymer to salt based PEG-salt. When a sample containing a plurality of analytes is poured onto the ATPS on the porous fiberglass paper, the pretreated porous fiberglass paper preferentially causes the analyte-containing ATPS component to flow ahead of the other ATPS component. Therefore, the targeted analyte is concentrated in the analyte-containing ATPS component and at the front of the fluid flow.

In one embodiment, the porous fiberglass paper is impregnated with ATPS which is made of micellar based surfactant-containing solutions. When a sample containing a plurality of analytes is poured onto the ATPS on the porous fiberglass paper, the impregnated porous fiberglass paper preferentially causes the analyte-containing ATPS component to flow ahead of the other ATPS component. Therefore, the targeted analyte is concentrated in the analyte-containing ATPS component at the front of the fluid flow.

In one embodiment, multiple ATPS components are incorporated into a porous material to control the concentration factors of target analyte (i.e., biomarker).

In one embodiment, a polymer/salt ATPS is implemented with the optimization in the ratios of the ATPS components to control the concentration factors.

In one embodiment, a polymer/polymer ATPS is implemented with the optimization in the ratios of the ATPS components to control the concentration factors.

In one embodiment, a micellar ATPS is implemented with the optimization in the ratios of the ATPS components to control the concentration factors.

In one embodiment, the ATPS embedded onto a porous material allows the concentration of biomolecules at the leading front of the fluid flow. The ratios of the ATPS components are adjusted to demonstrate concentration factors between 10 folds and 100 folds.

In one embodiment, the ATPS embedded in porous material is used with a blood sample, the concentration factors are between 10 folds and 100 folds.

In one embodiment, there are various ATPS systems including but are not limited to polymer-polymer (e.g. PEG-dextran), polymer-salt (e.g. PEG-salt), and micellar (e.g. Triton X-114). The first and/or second component comprises a polymer. Polymer includes but is not limited to polyalkylene glycols, such as hydrophobically modified polyalkylene glycols, poly(oxyalkylene)polymers, poly (oxyalkylene)copolymers, such as hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. In another embodiment, the first polymer comprises polyethylene glycol, polypropylene glycol, or dextran.

In one embodiment, the polymer concentration of the first component or second component is in the range of about 0.01% to about 90% by weight of the total weight of the aqueous solution (w/w). In various embodiments, the polymer solution is selected from a polymer solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the polymer solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

In one embodiment, the first and/or second component comprises a salt, the salt includes but is not limited to kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate. In another embodiment, the salt is selected from the group consisting of NaCl, Na3PO4, K3PO4, Na2SO4, potassium citrate, (NH4)2SO4, sodium citrate, sodium acetate and combinations thereof. Other salts, e g ammonium acetate, may also be used.

In one embodiment, the total salt concentration is in the range of 0.001 mM to 100 mM. A skilled person in the art will understand that the amount of salt needed to form an aqueous two-phase system will be influenced by molecular weight, concentration and physical status of the polymer.

In various embodiments, the salt phase is selected from a salt solution that is about 0.001% to 90% w/w. In various embodiments, the salt solution is selected from a salt solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the salt solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

In one embodiment, the first component and/or the second component in the ATPS comprises a solvent that is immiscible with water. In some embodiments, the solvent comprises a non-polar organic solvent. In some embodiments, the solvent comprises an oil. In some embodiments, the solvent is selected from pentane, cyclopentane, benzene, 1,4-dioxane, diethyl ether, dichloromethane, chloroform, toluene and hexane.

In one embodiment, the first component and/or second component in the ATPS comprises a micellar solution. In some embodiments, the micellar solution comprises a nonionic surfactant. In some embodiments, the micellar solution comprises a detergent. In some embodiments, the micellar solution comprises Triton-X. In some embodiments, the micellar solution comprises a polymer similar to Triton-X, such as Igepal CA-630 and Nonidet P-40. In some embodiments, the micellar solution consists essentially of Triton-X.

In one embodiment, the first component in the ATPS comprises a micellar solution and the second component in the liquid phase comprises a polymer. In one embodiment, the second component in the liquid phase comprises a micellar solution and the first component in the liquid phase comprises a polymer. In one embodiment, the first component in the liquid phase comprises a micellar solution and the second component in the liquid phase comprises a salt. In one embodiment, the second component in the liquid phase comprises a micellar solution and the first component comprises a salt. In one embodiment, the micellar solution is a Triton-X solution. In one embodiments, the first component comprises a first polymer and the second component comprises a second polymer. In one embodiment, the first/second polymer is selected from polyethylene glycol and dextran. In one embodiments, the first component comprises a polymer and the second component comprises a salt. In one embodiment, the second component comprises a polymer and the first component comprises a salt. In some embodiments, the first component comprises polyethylene glycol and the second component comprises potassium phosphate. In some embodiments, the second component comprises polyethylene glycol and the first component comprises potassium phosphate. In one embodiment, the first component comprises a salt and the second component comprises a salt. In one embodiments, the first component comprises a kosmotropic salt and the second component comprises a chaotropic salt. In some embodiments, the second component comprises a kosmotropic salt and the first component comprises a chaotropic salt.

In one embodiments, ratios of the first component to the second component are in the range of 1:1 to 1:1000. In some embodiments, the ratio of the first component to the second component is selected from a ratio of about 1:1, about 1:2, about 1:3, about 1:4, about 1:5, about 1:6, about 1:7, about 1:8, about 1:9, and about 1:10. In some embodiments the ratio of the first component to the second component is selected from a ratio of about 1:20, about 1:30, about 1:40, about 1:50, about 1:60, about 1:70, about 1:80, about 1:90, and about 1:100. In some embodiments the ratio of the first component to the second component is selected from a ratio of about 1:200, about 1:300, about 1:400, about 1:500, about 1:600, about 1:700, about 1:800, about 1:900, and about 1:1000.

In one embodiment, the ratio of the second component to the first component is selected from a ratio of about 1:1, about 1:2, about 1:3, about 1:4, about 1:5, about 1:6, about 1:7, about 1:8, about 1:9, and about 1:10. In some embodiments the ratio of the second component to the first component is selected from a ratio of about 1:20, about 1:30, about 1:40, about 1:50, about 1:60, about 1:70, about 1:80, about 1:90, and about 1:100. In some embodiments the ratio of the second component to the first component is selected from a ratio of about 1:200, about 1:300, about 1:400, about 1:500, about 1:600, about 1:700, about 1:800, about 1:900, and about 1:1000.

Downstream Processing of the Isolated Biomarkers

In various embodiments, the present invention can be used in combination with one or more processes or reagents for the purpose of washing and elution of the biomarkers retained in the porous matrix, or post-isolation treatment of the retained biomarker.

In one embodiment, after contacting the biomarker-containing solution with the ATPS, a washing buffer is applied on the ATPS, once or for multiple times, to wash off non-target biomarker or impurities from the porous matrix. Washing buffers may comprise solutions of varying ionic strength, pH values, or contain additives such as detergents. Examples of washing buffers include but are not limited to a solution of 20%-50% ethanol and 20%-50% isopropanol; a solution of about 0.1-4.0 M guanidinium hydrochloride, detergents and up to about 80% ethanol; or a solution of about 80% ethanol.

In one embodiment, target biomarker enters the porous matrix of the ATPS and flow to one end of the porous matrix. In one embodiment, target biomarker isolated by the present invention are eluted out of the porous matrix using appropriate elution butters or deionized water. In one embodiment, isolated target biomarker are not eluted but stored for future use in the porous matrix. For instance, after the isolation of biomarker using the present invention, the porous material (e.g. a paper) containing the target biomarker (e.g. a DNA biomarker) is dried and stored. In one embodiment, biomarker retained on the porous matrix can be eluted for further analysis or treatment. The selection of the elution buffer may depend on the contemplated use of the purified biomarker. Examples of suitable elution buffers for nucleic acid type of biomarkers includes, but are not limited to, Tris-EDTA (TE) buffer, aqua bidest and PCR buffer. In one embodiment, the purified analyte on porous paper is eluted in a tube containing TE buffer (10 mM Tris.Cl, 1 mM EDTA solution with pH 7.5), and the purified analyte is recovered in a relatively small volume, e.g., less than 10 μl.

Improvement of Diagnostic Procedures Using the Present Invention

Biomarkers obtained by the present method can be subject to a wide range of downstream applications such as detection or analysis of the biomarkers in forensic, diagnostic or therapeutic applications, and laboratory procedures such as sequencing, amplification, reverse transcription, labeling, digestion, blotting procedures and the like. It is expected that the present invention is able to improve the performance of downstream characterization or processing of the biomarkers.

In one embodiment, the present is capable of purifying and concentrating target biomarkers indicative of a disease present in a sample, the product obtained is subject to downstream diagnostic procedure requiring the detection or quantification of the target biomarkers. In particular, since the present invention can perform cell lysis and purification and concentration of target biomarkers in one single step with simple set up and quickly, regardless of the sample size or the amount of the target biomarkers in the sample, the present invention provides high quality samples containing the target biomarkers and thereby significantly improves the performance of diagnosis in terms of accuracy, sensitivity and efficiency. It is also expected that the present invention can reduce the signal-to-noise ratio and enhance the positive signal in downstream procedures since most of the impurities have been removed. False positive rate and false negative rate could also be lowered as a result.

In one embodiment, downstream applications of the purified biomarker include, but are not limited to, any detection, analytical or diagnostic procedures involving the detection or quantification of the purified biomarker. In one embodiment, detection, analytical or diagnostic procedures to be coupled with the present invention include but are not limited to any such procedure performed in commercial clinical laboratory, and laboratory procedures such as sequencing, amplification (e.g. PCR, RT-PCR, real-time PCR, and real-time RT-PCR), reverse transcription, labeling, digestion, blotting procedures, ELISA, RIA, immunoassays, enzymatic assays, GC/MS, proteomic-based approach, and the like. In one embodiment, the present invention is coupled with enzyme-linked immunosorbent assay (ELISA) and specific antibody-antigen. There are two huge benefits. First, the lengthy time spent in assessing conjugated enzyme activity via incubation with a substrate to produce a measurable product will be cut short. The present method for preparing the target analytes functions isothermally and based only on thermal dynamic principles. The whole sample preparation process takes only 10 minutes to about an hour instead of hours or even days in conventional ELISA procedures. Secondly, the low concentration of targeted biomolecules such as peptides, proteins, antibodies and hormones can be improved significantly by the prevent invention. The concentration can be improved by up to 10 folds to 100 folds and therefore it is possible to detect molecules which could not be detected due to their low abundance or interference by impurities in the sample.

In one embodiment, the present invention is coupled with polymerase chain reaction (PCR). In one embodiment, DNA molecules present in very minute amount or minute concentration (which can be due to large volume of the sample or minute amount of the DNA or both) is highly concentrated by the present invention. Originally minute concentration of DNA may not be detected and processed by existing sample preparation kits in the art which have strong requirements and limitations on sample sizes. After processed by the present invention, targeted DNA biomarkers can be concentrated by 10 folds to 1000 folds. Thus, the sample volume size is substantially reduced and the amplification and sensitivity of PCR test is much improved.

In one embodiment, biomarkers mentioned herein can be detected through any known method for the detection, such as high-pressure liquid chromatography, immunoassays, and an indicator rinsed by a chemical or enzymatic method. In an exemplary embodiment of an indicator rinse of the present disclosure, the rinse may further comprise one or more additional component as described herein. These additional components may include stabilizing agents, as well as Generally Recognized as Safe (GRAS) components.

In one embodiment, buffer solution used herein includes, but are not limited to, phosphate-buffered saline (PBS), Tris-EDTA (TE) buffer. In this invention, prefer buffer is PBS buffer 9.57 Mm (8 mM Sodium chloride, 0.2 mM Potassium chloride, 1.15 mM Sodium monohydrogen phosphate, 0.2 mM Potassium dihydrogen phosphate, solution with pH 7.35-7.65). In this invention, prefer buffer is TE buffer containing 2% bovine serum albumin (BSA), 0.1% Tween-20, 0.1% PEG and 20 mM Tris, pH 7.5 respectively.

In one embodiments, the present invention provides a method for accurate diagnosis of a disease, the method comprises the steps of:

(a) providing a sample solution comprising a target biomarker of said disease;

(b) providing a porous material embedded with components of an aqueous two-phase system (ATPS), wherein said components form two phase solutions when an aqueous solution travels through said porous material so that one phase solution travels faster than the other phase solution;

(c) allowing said porous material to wick said sample solution, wherein the target biomarker in the sample solution partitions into the faster moving phase solution and becomes concentrated at the front of the faster moving phase solution;

(d) colleting the target biomarker from the front of the faster moving phase solution, resulting in a final solution containing the target biomarker at a concentration at least 50-fold higher than the concentration of the target biomarker in said sample solution; and (e) subjecting said final solution to a diagnostic assay for detection or quantification of said target biomarker; wherein the accuracy of diagnosing said disease is significantly improved.

In one embodiment of the method described herein, the porous material is selected from the group consisting of fiber-glass paper, cotton-based paper, single-layer matrix paper and polyolefin foam pad.

In one embodiment of the method described herein, the ATPS components are selected from polymers, salts and surfactants.

In one embodiment of the method described herein, the polymers are selected from the group consisting of polyalkylene glycols, poly(oxyalkylene)polymers, poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, poly N-isopropylacrylamide, polyethylene glycol, polypropylene glycol and dextran.

In one embodiment of the method described herein, the salts are selected from the group consisting of kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, NaCl, $Na_3PO4$, $K_3PO_4$, $Na_2SO_4$, potassium citrate, $(NH_4)_2SO_4$, sodium citrate, sodium acetate, ammonium acetate, and any combination thereof.

In one embodiment of the method described herein, the surfactants are selected from the group consisting of nonionic surfactants, detergents, Triton-X, Igepal CA-630 and Nonidet P-40.

In one embodiment of the method described herein, the sample solution comprises one or more of blood, plasma, serum, urine, saliva, fecal matters and bodily discharges.

In one embodiment of the method described herein, the target biomarker is selected form the group consisting of nucleic acids, proteins, carbohydrates, lipids, metal ions, vitamins and metabolites.

In one embodiment of the method described herein, the nucleic acids are cell-free DNA or circulating tumor DNA.

In one embodiment of the method described herein, the target biomarker is selected form the group consisting of alpha-fetoprotein (AFP), Cancer Antigen (CA15-3), cancer Antigen (CA125), Prostate specific antigen BRCA1, Carcinoembryonic antigen, c-erb-2, P16, p53, Aldose reductase, Angiogenin, Annexin A1, B-cell activating factor (BAFF), B-cell lymphoma 2 (BCL2)-like 2, Beta Human chorionic gonadotropin, Ca15-3, Calcyclin, Calvasculin, Cathepsin D, Caveolin-1, Chromogranin A, Alpha-crystallin B chain (CRYAB), Endostatin, Eotaxin-2, Epithelial cell adhesion molecule (EpCAM), Ezrin, fatty acid binding protein 4 (FABP4), Galectin-3, γ-glutamylcysteine ligase regulatory chain (GCLR), Gelsolin, Glucose 6-phosphate (G6P), Glycoprotein 130 (gp130), Glutathione S-transferase Mu 1 (GSTM1), Hepsin, High-mobility group protein B1 (HMGB-1), Insulin-like growth factor binding protein 1 (IGFBP-1), Insulin-like growth factor binding protein 4 (IGFBP-4), Insulin-like growth factor binding protein 5 (IGFBP-5), Insulin-like growth factor binding protein 6 (IGFBP-6), LGL, latency associated peptide (LAP), macrophage stimulating protein (MSP), MHC class I polypeptide-related sequence A (MICA), Nucleoside diphosphate kinase B (NME2), Neuron-specific Enolase (NSE), Osteopontin, Osteoprotegerin, Pepsinogen, Peroxiredoxin, Phosphoserine aminotransferase (PSAT1), Prostate Specific Antigen, Receptor tyrosine-protein kinase erbB-3 (ErbB3), Serpin B3, Vascular smooth muscle cell growth factor R2 (VSGF R2/KDR), Vascular endothelial growth factor R3 (VEGF R3/Flt-4), Thyroglobulin, Tyrosine kinase with immunoglobulin-like and EGF-like domains 2 (TIE-2), Tissue plasminogen activator (tPA), Transforming growth factor beta (TGF-β1), Tumor necrosis factor receptor 1 (TNF-R1), urokinase-type Plasminogen Activator (uPA), urokinase-type Plasminogen Activator Receptor (uPAR), Brcal, Brcall, kallikreins, e-cadherin, Hox peptide, and Engrailed-2.

In one embodiment of the method described herein, the target biomarker is concentrated by up to 100-fold.

In one embodiment of the method described herein, the disease is cancer.

In one embodiment of the method described herein, the diagnostic assay is selected form the group consisting of Enzyme-Linked Immune Sorbent Assay (ELISA), Polymerase Chain Reaction (PCR), Radioimmunoassay (RIA), proteomic-based approach, blotting procedure, immunoassay, enzymatic assay and GC/MS.

This invention will be better understood by reference to the examples which follow. However, one skilled in the art will readily appreciate that the examples provided are merely for illustrative purposes and are not meant to limit the scope of the invention which is defined by the claims following thereafter.

EXAMPLES

Example 1—Embedding ATPS on with Porous Material

The formulated ATPS components, 20% (w/w) PEG 4600, 2% (w/w) SDS, 16% (w/w) Triton-X114 and 18.5% (w/w) $Na_2SO_4$, were dehydrated onto the porous paper (including fiberglass paper, cotton-based paper, a proprietary single-layer matrix paper, and a polyolefin foam pad, of width 2.2 cm and variable lengths). PEG solution (in DI $H_2O$) was added to the narrow end of each porous material. 50 uL of a Tris-buffered solution containing 2% bovine serum albumin (BSA), 0.1% Tween-20, and 0.1% PEG, 20 mM Tris pH 7.5 respectively) was added immediately adjacent to the first solution.

The above porous materials with embedded ATPS were then dried in a lyophilizer for 1 hour and cut into 0.5 cm strips lengthwise (new dimensions: 4 cm×0.5 cm). Pieces were then stacked (four strips per stack) and cut at one end from the corner to a spot 0.5 cm from the end (forming a triangle, see FIG. 1). The ATPS-embedded porous materials were then placed in an indicator-containing (colloidal gold) buffer solution with salt (in this case, potassium phosphate) in PBS (overall pH 7.4), resulting in capillary action-mediated flow.

Example 2—Concentration of Circulating Cell Free DNA (ccfDNA) in Plasma Using the Present Invention Plasma samples were collected from patients and healthy individuals. ccfDNA was purified from the plasma sample using the present invention or QIAamp Circulating Nucleic Acid Kit (QIAGEN). As described in the previous examples, ATPS-paper stack and the control stack were immersed in the plasma samples, and wicked for approximately 2 minutes until the solution reached the top. The top was extracted and subjected to ethanol precipitation for Nanodrop analysis. The results were compared with the results obtained from QIAamp Circulating Nucleic Acid Kit (QIAGEN). Table 1 shows that the present invention can isolate cfDNA from plasma samples obtained from patients or healthy subjects at a higher yield than the commercial kit.

TABLE 1

Isolation and concentration of ccfDNA from serum samples obtained from patients and healthy subjects using the present method or QIAamp Circulating Nucleic Acid Kit

| DNA | Isolation method | Yield (ng) |
|---|---|---|
| Patient sample | Present ATPS method | 184 |
| | QIAamp Circulating Nucleic Acid Kit | 89 |
| Healthy control | Present ATPS method | 27 |
| | QIAamp Circulating Nucleic Acid Kit | 5 |

Example 3—Concentration of Alpha-Fetoprotein (AFP) in Serum Using the Present Invention Serum samples were collected from patients and healthy individuals. Alpha-fetoprotein (AFP) was purified and concentrated from the serum sample using the present invention and the Alpha-Fetoprotein (AFP) ELISA Kit provided by BioSupply Ltd, 11 The Grove, Shipley, BD18 4LD. alpha-fetoprotein (AFP) standard was spiked into one set of the serum sample for comparison.

As described in Example 1, ATPS-paper stack and the control stack were immersed in the serum samples, and wicked for approximately 2 minutes until the solution reached the top. The top was extracted and subjected to analysis. Table 2 shows that the present invention can concentrate alpha-fetoprotein (AFP) from serum samples obtained from patients or healthy individuals.

AFP standard was prepared by dissolving AFP (Sigma Aldrich, Product No. A 8452) with deionized water which is 50 ng/L.

TABLE 2

Isolation and concentration of alpha-fetoprotein (AFP) from serum samples obtained from patients or healthy individuals.

| Test | Method | ATPS-paper stack | Control stack | Concentration fold |
|---|---|---|---|---|
| Healthy control | Present Method | 1000 ng/L | 10 ng/L | 100-fold |
| | ELISA KIT | 600 ng/L | 10 ng/L | 60-fold |
| Patient sample | Present Method | 50 ug/L | 500 ng/L | 100-fold |
| | ELISA KIT | 27.5 ug/L | 500 ng/L | 55-fold |

Example 4—Concentration of Cancer Antigen (CA15-3) in Serum Using the Present Invention and Cancer Antigen 15-3 (CA15-3) Elisa Kit Serum samples were collected from patients and healthy individuals. Cancer Antigen (CA15-3) was purified and concentrate from the serum sample using the present invention and the Cancer Antigen 15-3 (CA15-3) ELISA Kit provided by BioSupply Ltd, 11 The Grove, Shipley, BD18 4LD. Cancer Antigen (CA15-3) standard was spiked into one set of the serum sample for comparison.

As described in Example 1, ATPS-paper stack and the control stack were immersed in the serum samples, and wicked for approximately 2 minutes until the solution reached the top. The top was extracted and subjected to analysis. Table 3 shows that the present invention can concentrate Cancer Antigen 15-3 from serum samples obtained from patients or healthy individuals.

Cancer Antigen 15-3 (CA15-3) standard was prepared by dissolving Cancer Antigen 15-3 (commercially available from Fitzgerald Industries International, Inc. (CA15-3 MAb M8071022) with deionized water which is 25 kU/L.

TABLE 3

Isolation and concentration of Cancer Antigen 15-3 from serum samples obtained from patients or healthy individuals.

| Test | Method | ATPS-paper stack | Control stack | Concentration fold |
|---|---|---|---|---|
| Healthy control | Present Method | 2500 kU/L | 25 kU/L | 100-fold |
| | ELISA KIT | 1250 kU/L | 25 kU/L | 50-fold |
| Patient sample | Present Method | 3100 kU/L | 31 kU/L | 100-fold |
| | ELISA KIT | 1550 kU/L | 31 kU/L | 50-fold |

What is claimed is:

1. A method for accurate diagnosis of a disease, comprising the steps of:

(a) providing a sample solution comprising a target biomarker of said disease;

(b) providing a porous material embedded with components of an aqueous two-phase system (ATPS), wherein said components form two phase solutions when an aqueous solution travels through said porous material so that one phase solution travels faster than the other phase solution;

(c) allowing said porous material to wick said sample solution, wherein the target biomarker in the sample solution partitions into the faster moving phase solution and becomes concentrated at the front of the faster moving phase solution;

(d) applying a washing buffer on the ATPS to wash off impurities from said porous material, wherein the target biomarker is retained in the porous material;

(e) drying and storing said porous material containing the target biomarker;

(f) eluting the target biomarker from the front of the faster moving phase solution by an elution buffer, resulting in a final solution containing the target biomarker; and (g) subjecting said final solution to a diagnostic assay for detection and quantification of said target biomarker;

wherein the target biomarker is selected from the group consisting of alpha-fetoprotein (AFP), Cancer Antigen (CA15-3), and cell-free DNA, and wherein said ATPS components are selected from polymers, salts and surfactants.

2. The method of claim 1, wherein the concentration of said target biomarker in said final solution is at least 50-fold higher than the concentration of the target biomarker in said sample solution.

3. The method of claim 1, wherein the porous material is selected from the group consisting of fiber-glass paper, cotton-based paper, single-layer matrix paper and polyolefin foam pad.

4. The method of claim 1, wherein said polymers are selected from the group consisting of polyalkylene glycols, poly(oxyalkylene)polymers, poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, poly N-isopropylacrylamide, polyethylene glycol, polypropylene glycol and dextran.

5. The method of claim 1, wherein said salts are selected from the group consisting of kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, NaCl, $Na_3PO4$, $K_3PO_4$, $Na_2SO_4$, potassium citrate, $(NH_4)_2SO_4$, sodium citrate, sodium acetate, ammonium acetate, and any combinations thereof.

6. The method of claim 1, wherein said surfactants are selected from the group consisting of nonionic surfactants, detergents, Triton-X, Igepal CA-630 and Nonidet P-40.

7. The method of claim 1, wherein the sample solution comprises one or more of blood, plasma, serum, urine, saliva, fecal matters and bodily discharges.

8. The method of claim 1, wherein the target biomarker is concentrated by up to 100-fold.

9. The method of claim 1, wherein the disease is cancer.

10. The method of claim 1, wherein the diagnostic assay is selected form the group consisting of Enzyme-Linked Immune Sorbent Assay (ELISA), Polymerase Chain Reaction (PCR), Radioimmunoassay (RIA), proteomic-based approach, blotting procedure, immunoassay, enzymatic assay and GC/MS.

11. The method of claim 1, wherein said ATPS components comprise polyethylene glycol, SDS, Triton-X114 and $Na_2SO_4$.

12. The method of claim 11, wherein said polyethylene glycol is PEG4600.

13. The method of claim 1, wherein said ATPS components comprise 20% (w/w) PEG4600, 2% (w/w) SDS, 16% (w/w) Triton-X114 and 18.5% (w/w) $Na_2SO_4$.

* * * * *